United States Patent
Hwang et al.

(10) Patent No.: US 9,262,685 B2
(45) Date of Patent: Feb. 16, 2016

(54) METHOD AND APPARATUS FOR REPRESENTING CHANGES IN SHAPE AND LOCATION OF ORGAN IN RESPIRATION CYCLE

(71) Applicant: Samsung Electronics Co., Ltd., Suwon-si (KR)

(72) Inventors: Young-kyoo Hwang, Seoul (KR); Na-hyup Kang, Seoul (KR); Do-kyoon Kim, Seongnam-si (KR); Jung-bae Kim, Hwaseong-si (KR); Young-taek Oh, Seoul (KR); Hyong-euk Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 33 days.

(21) Appl. No.: 14/093,866

(22) Filed: Dec. 2, 2013

(65) Prior Publication Data

US 2014/0218359 A1  Aug. 7, 2014

(30) Foreign Application Priority Data

Feb. 6, 2013  (KR) ......................... 10-2013-0013493

(51) Int. Cl.
| | |
|---|---|
| *G06T 15/00* | (2011.01) |
| *G06K 9/46* | (2006.01) |
| *G06K 9/62* | (2006.01) |
| *G06T 7/00* | (2006.01) |

(Continued)

(52) U.S. Cl.
CPC .............. *G06K 9/4604* (2013.01); *A61B 8/483* (2013.01); *G06K 9/6206* (2013.01); *G06T 7/0032* (2013.01); *G06T 7/0083* (2013.01); *G06T 7/0089* (2013.01); *A61B 8/44* (2013.01); *G06K 2209/05* (2013.01); *G06T 2207/10136* (2013.01); *G06T 2207/20124* (2013.01); *G06T 2207/30096* (2013.01); *G06T 2207/30101* (2013.01)

(58) Field of Classification Search
CPC . G06K 9/4604; G06K 9/201; G06K 2209/05; G06K 9/6206; G06T 7/00
USPC .................... 345/419, 420; 703/2, 6; 382/131
See application file for complete search history.

(56) References Cited

U.S. PATENT DOCUMENTS

| | | | |
|---|---|---|---|
| 8,027,430 B2* | 9/2011 | Nord et al. ...................... | 378/65 |
| 8,751,200 B2* | 6/2014 | Takai et al. ...................... | 703/2 |

(Continued)

FOREIGN PATENT DOCUMENTS

| | | |
|---|---|---|
| JP | 2003-144412 | 5/2003 |
| KR | 10-2009-0127101 | 12/2009 |

(Continued)

*Primary Examiner* — Phu K Nguyen
(74) *Attorney, Agent, or Firm* — NSIP Law

(57) ABSTRACT

Provided is a method of generating a model, the method including generating a first model representing a change in the location or the shape of the region of interest during the respiration cycle, using diagnostic images that are obtained at two points of time in the respiration cycle and that represent the region of interest; extracting shape information of one or more tissues included in the region of interest at a shape information extractor, using a 3D ultrasound image that is obtained at one point of time in the respiration cycle; determining a characteristic point of the 3D ultrasound image corresponding to a characteristic point of the first model by matching the first model with the extracted shape information; and generating a second model by updating the first model with the determined characteristic point.

18 Claims, 6 Drawing Sheets

(51) Int. Cl.
*A61B 8/08* (2006.01)
*A61B 8/00* (2006.01)

(56) References Cited

U.S. PATENT DOCUMENTS 8,849,003 B2 * 9/2014 Punithakumar et al. ...... 382/131
8,849,633 B2 * 9/2014 Core et al. ...................... 703/6
2009/0034819 A1 2/2009 Nord et al.

FOREIGN PATENT DOCUMENTS

| KR | 10-2010-0025431 | 3/2010 |
| KR | 10-2011-0018573 | 2/2011 |

* cited by examiner

METHOD AND APPARATUS FOR REPRESENTING CHANGES IN SHAPE AND LOCATION OF ORGAN IN RESPIRATION CYCLE

CROSS-REFERENCE TO RELATED APPLICATIONS

This application claims the benefit under 35 U.S.C. §119(a) of Korean Patent Application No. 10-2013-0013493, filed on Feb. 6, 2013, in the Korean Intellectual Property Office, the entire disclosure of which is incorporated herein by reference for all purposes.

BACKGROUND

1. Field

The following description relates to methods and apparatuses for generating a model representing deformation of a shape and a location of an organ in a respiration cycle.

2. Description of the Related Art

A high-intensity focused ultrasound (HIFU) treatment is an operation technique to remove and treat a tumor by radiating HIFU to a tumor part (focus) to be treated and causing focal destruction or necrosis of tumor tissue.

Removing a lesion by using the HIFU is a widely used treatment techniques because it is possible to treat a human body without directly cutting into it. When the HIFU is radiated to the lesion from outside of the human body, a location of the lesion changes due to movement of the human body. For example, if a patient respires during therapy, the location of the lesion changes depending on respiration. Thus, a location (focus) to which the HIFU is radiated should also change. A method of tracking the location of the lesion that is changed by the movement of the human body and radiating the HIFU has been studied.

The location of an organ changes depending on respiration and thus a shape of the organ also changes, i.e., there is a close relation between the respiration and changes in the location and shape of the organ. In addition, since the respiration changes periodically, it is possible to estimate current locations of the organ and the lesion by using respiration signals of a patient if locations of the organ and the lesion depending on the respiration of the patient are known before therapy.

However, diagnostic images, such as, for example magnetic resonance (MR) or computed tomography (CT) images are captured at the full expiration (FE) and at the full inspiration (FI) of the patient to obtain changes in the location and shape of the organ depending on a change in the respiration of the patient. In this case, there are some cases where diagnostic images, such as, for example the desired MR or CT images are not obtained because the patient fails to temporarily stop respiration or a proper time period in which a contrast medium stays in a blood vessel cannot be calculated.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method of generating a model, the method including generating a first model representing a change in the location or the shape of the region of interest during the respiration cycle, using diagnostic images that are obtained at two points of time in the respiration cycle and that represent the region of interest; extracting shape information of one or more tissues included in the region of interest at a shape information extractor, using a 3D ultrasound image that is obtained at one point of time in the respiration cycle; determining a characteristic point of the 3D ultrasound image corresponding to a characteristic point of the first model by matching the first model with the extracted shape information; and generating a second model by updating the first model with the determined characteristic point.

The extracting of the shape information may include performing a flatness test to determine whether the tissue is flat or a vesselness test to determine whether the tissue has a tube shape, and extracting shape information of the tissue from the 3D ultrasound image.

The tissue may include a diaphragm or a blood vessel.

The determining of the characteristic point may include performing rigid registration on the first model and the extracted shape information; performing non-rigid registration by using a result of the rigid registration; and determining the characteristic point by using a result of the non-rigid registration.

The generating of the second model may include calculating a physical property of a tissue included in the region of interest, using the diagnostic images; matching the characteristic point with a vertex of the first model, by using the physical property; and generating the second model by using a result of the matching.

The generating of the first model may include segmenting surface information of the tissue that is represented on each of the diagnostic images; and performing interpolation by using the segmented surface information.

The tissue may include a lesion.

The two points of time in the respiration cycle may be a full inspiration time and a full expiration time.

In another general aspect, an apparatus for generating a model, the apparatus including a first model generator configured to generate a first model representing a change in a location or a shape of a region of interest during a respiration cycle, using diagnostic images that are obtained at two points of time in the respiration cycle and that represent the region of interest; a shape information extractor configured to extract shape information of one or more tissues included in the region of interest, using a 3D ultrasound image that is obtained at one point of time in the respiration cycle; a characteristic point determiner configured to determine a characteristic point of the 3D ultrasound image corresponding to a characteristic point of the first model; and a second model generator configured to generate a second model by updating the first model with the determined characteristic point.

The shape information extractor may be configured to perform a flatness test to determine whether the tissue is flat or a vesselness test to determine whether the tissue has a tube shape, and to extract shape information of the tissue from the 3D ultrasound image.

The tissue may include a diaphragm or a blood vessel.

The characteristic point determiner may be configured to perform rigid and non-rigid registration on the first model and the extracted shape information and to determine the characteristic point by using results of the rigid and non-rigid registration.

The second model generator may be configured to calculate a physical property of a tissue included in the region of interest by using the diagnostic images, match the characteristic point with a vertex of the first model by using the calculated physical property, and generate the second model using a result of the matching.

The first model generator may be configured to segments surface information of a tissue that is represented on each of the diagnostic images and perform interpolation by using the segmented surface information.

The tissue may include a lesion.

The two points of time in the respiration cycle may be a full inspiration time and a full expiration time.

A storage may be configured to store the first model and the second model.

Other features and aspects will be apparent from the following detailed description, the drawings, and the claims.

Figure 1:
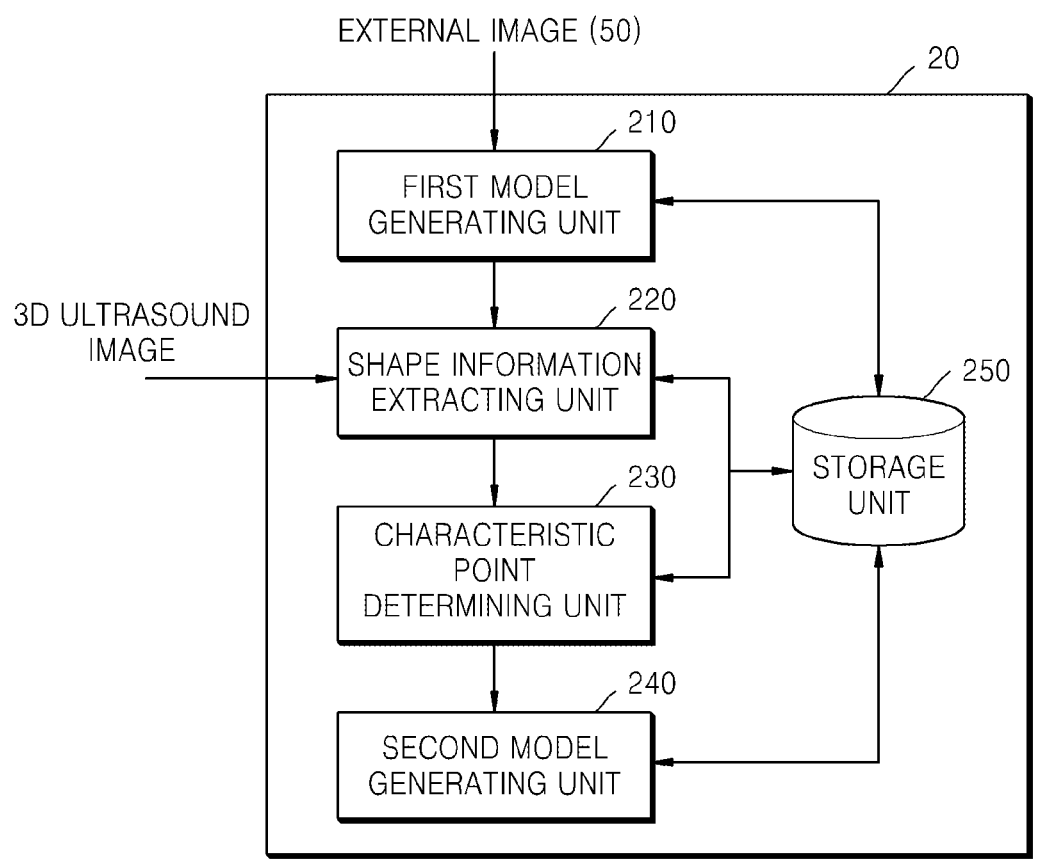
FIG. 1 is a diagram illustrating an example of an image processing apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be apparent to one of ordinary skill in the art. Also, descriptions of well-known functions and constructions may be omitted for increased clarity and conciseness.

FIG. 1 is a diagram illustrating an example of an image processing device 20. Referring to FIG. 1, the image processing device 20 includes a first model generating unit 210, a shape information extracting unit 220, a characteristic point determining unit 230, a second model generating unit 240, and a storage unit 250. Only components related to the present example are shown in the image processing device 20 of FIG. 1. Thus, those of ordinary skill in the art may understand that general components other than components shown in FIG. 1 may be further included. For example, the image processing device 20 may include an interface unit (not illustrated). The interface unit may be responsible for inputting and outputting input information regarding a user and an image. The interface unit may include a network module for connection to a network and a universal serial bus (USB) host module for forming a data transfer channel with a mobile storage medium, depending on a function of the image processing device 20. In addition, the interface unit includes an input/output device such as a mouse, a keyboard, a touch screen, a monitor, a speaker, and a software module for running the input/output device.

In addition, the first model generating unit 210, the shape information extracting unit 220, the characteristic point determining unit 230, the second model generating unit 240, and the storage unit 250 of the image processing device 20 shown in FIG. 1 may correspond to one or a plurality of processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processor may be implemented as an array of numerous logic gates and may also be implemented as a combination of a general-purpose microprocessor with a memory unit that stores a program that may be executed by the microprocessor. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors. In addition, those of ordinary skill in the art may understand that the one or more processing devices may be implemented in other forms of hardware.

The first model generating unit 210 uses diagnostic images, such as, for example magnetic resonance (MR) images or computer tomography (CT) images representing a region of interest (30 of FIG. 6) obtained at two points of time in a respiration cycle of a subject to generate a first model that represents a change in a location or a shape of the region of interest in the respiration cycle. In this case, the two points of time in the respiration cycle of the subject include a point of time of the full inspiration (FI) and a point of time of the full expiration (FE).

For example, the first model generating unit 210 segments surface information of a tissue that is represented on each of the diagnostic images, such as, for example an MR or CT image obtained at the point of time of the FI or an MR or CT image obtained at the point of time of the FE. In this case, the diagnostic image, such as, for example, MR or CT image indicates an image that includes anatomical information of tissues forming the region of interest and the tissues may include lesion tissues. In addition, the first model generating unit 210 performs interpolation using the segmented surface information to generate models.

Model means a set of images that represents a deformation in a location or a shape of the region of interest in the respiration cycle of the subject. The first model generating unit 210 may obtain a diagnostic image, such as, for example an MR or CT image (hereinafter, referred to as an external image (40 of FIG. 6)) directly from an external image capturing device or the storage unit 250.

Figure 2:
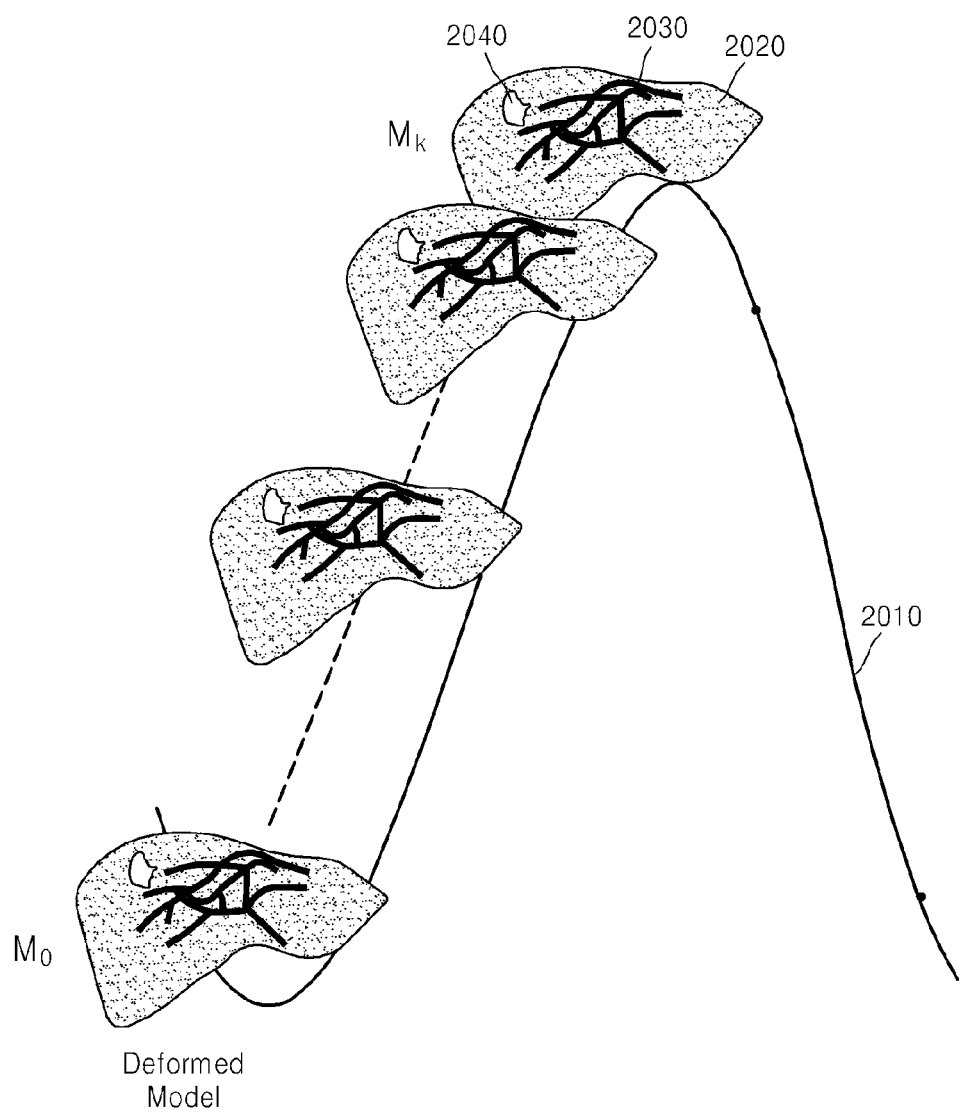
FIG. 2 is a diagram illustrating an example of how a first model generating unit operates.

FIG. 2 is diagram illustrating an example of how a first model generating unit 210 operates. The first model generating unit 210 segments surface information of tissues that are included in a region of interest (30 of FIG. 6) represented in an external image (40 of FIG. 6) obtained at a point of time Mk of a FI in a respiration cycle 2010 of a subject. For example, if it is assumed that the region of interest represented in the external image is a liver 2020 of the subject, the first model generating unit 210 segments a surface of the liver 2020 and those of blood vessels 2030 distributed in the liver. In addition, if a lesion 2040 exists in the liver 2020 of the subject, the first model generating unit 210 also segments a surface of the lesion 2040. In this case, the surface may mean an outline of a tissue. In addition, the first model generating unit 210 segments surface information of tissues that are included in a region of interest represented in an external image obtained at a point of time Mo of a FE in the respiration cycle of the subject, in the same way as that described above. Since those skilled in the art may understand how the first model generating unit 210 segments surface information of tissues represented in the external image, related detailed descriptions regarding how to segment will not be provided.

Subsequently, the first model generating unit 210 performs interpolation using the segmented surface information. For example, the first model generating unit 210 may perform interpolation using Bezier curve interpolation and the like. The first model generating unit 210 performs interpolation between the surface information pieces segmented from tissues having the same shapes. For example, the first model generating unit 210 performs interpolation using information about a surface of the blood vessel 2030 segmented from an image at the point of time Mk of the FI and information about the surface of the same blood vessel 2030 segmented from an image at a point of time Mo of a FE.

Since the first model generating unit 210 performs interpolation on the same regions in the two images as described above, it is possible to generate, for the respiration cycle 2010, a model representing changes in a location and a shape of an organ or a lesion that is included a region of interest. Since those skilled in the art may understand how the first model generating unit 210 performs interpolation (for example, Bezier curve interpolation), related detailed descriptions regarding how to segment will not be provided.

Referring back to FIG. 1, the first model generating unit 210 transmits a generated model to the storage unit 250. In this case, the generated model may have a mesh-shaped image in which surface information of tissues included in the region of interest is represented.

Figure 6:
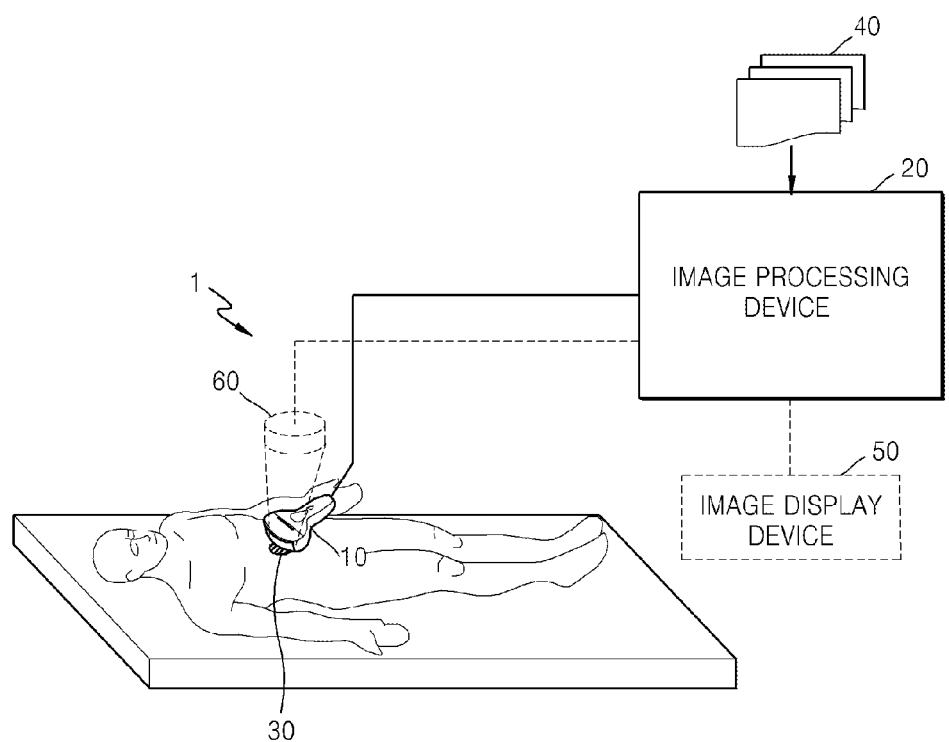
FIG. 6 is a diagram illustrating an example of an environment and system using a model generating system.

Accuracy of the model generated by the first model generating unit 210 depends on the precision of external images (40 of FIG. 6). Because the external images are obtained at points of time of FI and FE, if a subject (e.g. patient) fails to temporarily stop respiration, it may not be possible to obtain precise external images at the points of time of the FI and FE. In addition, if a proper time period for which contrast media stays in a blood vessel in the subject is not calculated, it may not be possible to obtain precise external images. In such a case, a first model generated using imprecise external images by the first model generating unit 210 may not accurately represent changes in a shape and a location of a region of interest in a respiration cycle of a subject. Thus, the image processing device 20 generates a second model which is produced by updating the first model using a 3D ultrasound image obtained at a point of time when the external image is not precisely obtained. Accordingly, it is possible to accurately generate a model representing changes in a shape and a location of tissues in a respiration cycle of a subject that form a region of interest.

The shape information extracting unit 220 uses a 3D ultrasound image representing a region of interest obtained at a point of time in a respiration cycle to extract shape information of one or more tissues, such as, for example a diaphragm or a blood vessel, which is included in the region of interest.

In addition, the shape information may include information about a thickness, length, and/or shape of the tissue. In addition, the point of time in the respiration cycle means a point of time when the imprecise external image is obtained.

For example, the shape information extracting unit 220 may extract shape information of one or more tissues included in a region of interest from a 3D ultrasound image generated using a diagnostic ultrasound probe (10 of FIG. 6). The 3D ultrasound image may be an image which the diagnostic ultrasound probe (10 of FIG. 6) has directly captured, and an image generating unit (not shown) in the image processing device 20 may also generate the 3D ultrasound image of a region of interest using electrical pulse signals transmitted from the diagnostic ultrasound probe (10 of FIG. 6). Since those skilled in the art may understand how to generate the 3D ultrasound image, related detailed descriptions regarding how to generate the 3D ultrasound image will not be provided. The shape information extracting unit 220 performs a flatness test to determine whether a tissue is flat or a vesselness test to determine whether the tissue has a tube shape, and extracts shape information of tissues or vessels from a 3D ultrasound image.

A diaphragm on a 3D ultrasound image is generally formed as a plate-shaped surface. The diaphragm on the 3D ultrasound image, such as, for example, a 3D B-mode image, exists across a significantly wide area and the number of voxels forming the diaphragm is also large. Thus, the shape information extracting unit 220 may perform a flatness test to extract information about the diaphragm from the 3D ultrasound image. For example, the shape image extracting unit 220 may remove parts except for the diaphragm from the 3D ultrasound image.

The shape information extracting unit 220 calculates flatness $u(v)$ at each voxel point forming the 3D ultrasound image through Hessian analysis. In this case, $u(v)$ has the condition $0 \leq u(v) \leq 1$.

The shape information extracting unit 220 calculates Hessian matrix $H_\sigma$ through Expression 1 below.

$$H_\sigma = \begin{bmatrix} I_{xx} & I_{xy} & I_{xz} \\ I_{yx} & I_{yy} & I_{yz} \\ I_{zx} & I_{zy} & I_{zz} \end{bmatrix} \quad \text{Expression 1}$$

In Expression 1 above, the subscript x, y, and z mean coordinate axes based on any origin point on the 3D ultrasound image. Each element forming the matrix is defined as Expressions 2 and 3 below.

$$I_{\alpha\beta}(x) = \delta^2 \frac{\partial^2 G(x, \sigma)}{\partial \alpha \partial \beta} * I(x) \quad \text{Expression 2}$$

In Expression 2 above, the term I represents a voxel forming the 3D ultrasound image.

$$G(x, \sigma) = \frac{1}{\sqrt{(2\pi\sigma^2)^3}} e^{-\frac{\|x\|^2}{2\sigma^2}} \quad \text{Expression 3}$$

In Expressions 2 and 3 above, $\sigma$ represents standard deviation.

Subsequently, the shape information extracting unit 220 uses the calculated Hessian matrix $H_\sigma$ to calculate eigen values ($\lambda_1$, $\lambda_2$, $\lambda_3$) corresponding to directional components of an eigen vector of the Hessian matrix $H_\sigma$ through eigen decomposition.

Figure 3:
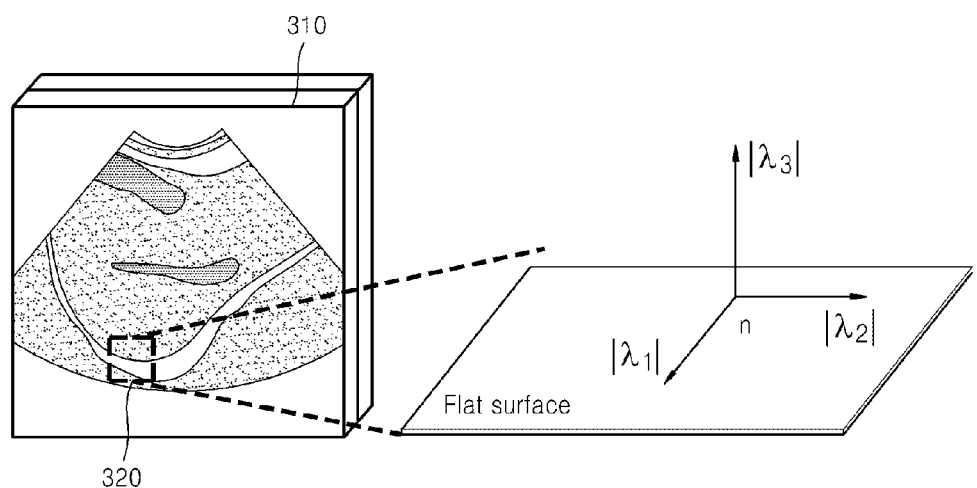
FIG. 3 is a diagram illustrating a conceptual view of Hessian matrix analysis that a shape information extracting unit performs as a process of a flatness test.

FIG. 3 is a diagram illustrating a conceptual view of Hessian matrix analysis that a shape information extracting unit 220 performs as a process of a flatness test.

If any voxel point v considered as a flat image exists on a 3D ultrasound image 310, the eigen values at the point 320 are as follows. The eigen value $\lambda_3$ meaning a variation in a normal direction becomes largest, the remaining eigen values $\lambda_1$ and $\lambda_2$ meaning variations in horizontal directions becomes values that are close to substantially zero at the point 320. Thus, the flatness u(v) calculated by the shape information extracting unit 220 is the same as Expression 4 below.

$$u(v) = \phi_1(v)\phi_2(v)\phi_3(v)/\phi_{3max}(v) \quad \text{Expression 4}$$

In Expression 4 above, $\phi_1(v)$, $\phi_2(v)$ and $\phi_3(v)$ are respectively defined as Expressions 5 to 7 below.

$$\phi_1(v) = \left(1 - \frac{\lambda_1(v)}{\lambda_3(v)}\right)^2 \quad \text{Expression 5}$$

$$\phi_2(v) = \left(1 - \frac{\lambda_2(v)}{\lambda_3(v)}\right)^2 \quad \text{Expression 6}$$

$$\phi_3(v) = \sum_i \lambda_i(v)^2 \quad \text{Expression 7}$$

Referring back to FIG. 1, the shape information extracting unit 220 may consider voxel points with a larger value than a certain threshold at each voxel point forming the 3D ultrasound image, as voxel points representing the diaphragm, by using the flatness u(v) calculated through the above-described Hessian matrix analysis. That is, the shape information extracting unit 220 may remove voxel points with a smaller value than a certain threshold at each voxel point forming the 3D ultrasound image, through the flatness test.

In addition, a blood vessel on the 3D ultrasound image generally has a straight line shape and a tube-shaped surface. In addition, the blood vessel on the 3D ultrasound image, such as, for example in a 3D B-mode image, exists over a significantly wide area and the number of voxels forming the blood vessel is also large. Thus, the shape information extracting unit 220 may perform a vesselness test to extract information about the blood vessel from the 3D ultrasound image. For example, the shape information extracting unit 220 may remove parts other than the blood vessel from the 3D ultrasound image.

Figure 4:
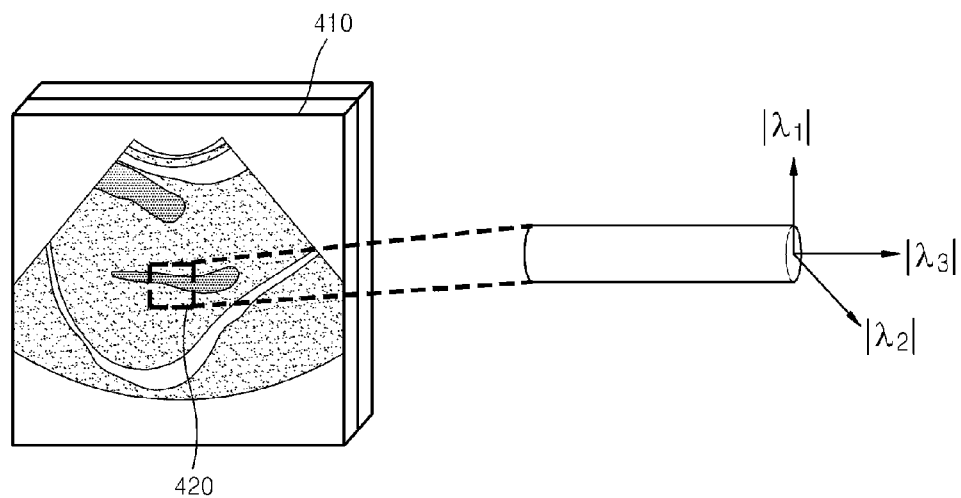
FIG. 4 is a diagram illustrating a conceptual view of Hessian matrix analysis that a shape information extracting unit performs through a vesselness test.

FIG. 4 is a diagram illustrating a conceptual view of Hessian matrix analysis that a shape information extracting unit 220 performs through a vesselness test. The shape information extracting unit 220 performs the vesselness test on voxels forming a 3D ultrasound image in a manner similar to how the flatness test is performed. The shape information extracting unit 220 calculates the eigen values of the Hessian matrix described above to perform the vesselness test.

If a 3D ultrasound image 410 has a voxel point n considered as a straight line-shaped image, sizes of the eigen values at the voxel point 420 are as follows. The eigen value $\lambda_3$ meaning a variation in a moving direction of a straight line becomes smallest, and the other eigen values $\lambda_1$ and $\lambda_2$ meaning variations in the other directions have very large values as compared to the eigen value $\lambda_3$.

Thus, if the size of the smallest eigen value $\lambda_3$ at a specific voxel point n is smaller than a predefined threshold, the shape information extracting unit 220 may determine that the voxel point has one directionality, and may thus consider that the voxel point 420 belongs to a blood vessel. The shape information extracting unit 220 may remove, through the vesselness test, voxel points having larger values than a certain threshold at each voxel point that forms the 3D ultrasound image.

Referring back to FIG. 1, the shape information extracting unit 220 transmits the extracted shape information to the characteristic point determining unit 230. In addition, the shape information extracting unit 220 may also transmit the extracted shape information to the storage unit 250. The extracted shape information means an image in which parts other than a part representing a shape of an extracted tissue have been removed from the 3D ultrasound image.

The characteristic point determining unit 230 determines a characteristic point on the 3D ultrasound image corresponding to a characteristic point of a first model through the matching of the first model with the extracted shape information. For example, the characteristic point determining unit 230 matches the first model transmitted from the storage unit 250 with shape information transmitted from the shape information extracting unit 220 to determine the characteristic point on the 3D ultrasound image that corresponds to the characteristic point of the first model. The characteristic point determining unit 230 may obtain information about a location where a characteristic point corresponding to that of the first model exists on the 3D ultrasound image.

The characteristic point determining unit 230 performs rigid registration of the first model with the shape information and performs non-rigid registration using a rigid matched result. In addition, the characteristic point determining unit 230 determines the characteristic point of the 3D ultrasound image using a result of the non-rigid registration.

FIGS. 5A to 5C are diagrams illustrating conceptual schematic views of rigid registration and non-rigid registration which a characteristic point determining unit 230 performs.

Figure 5:
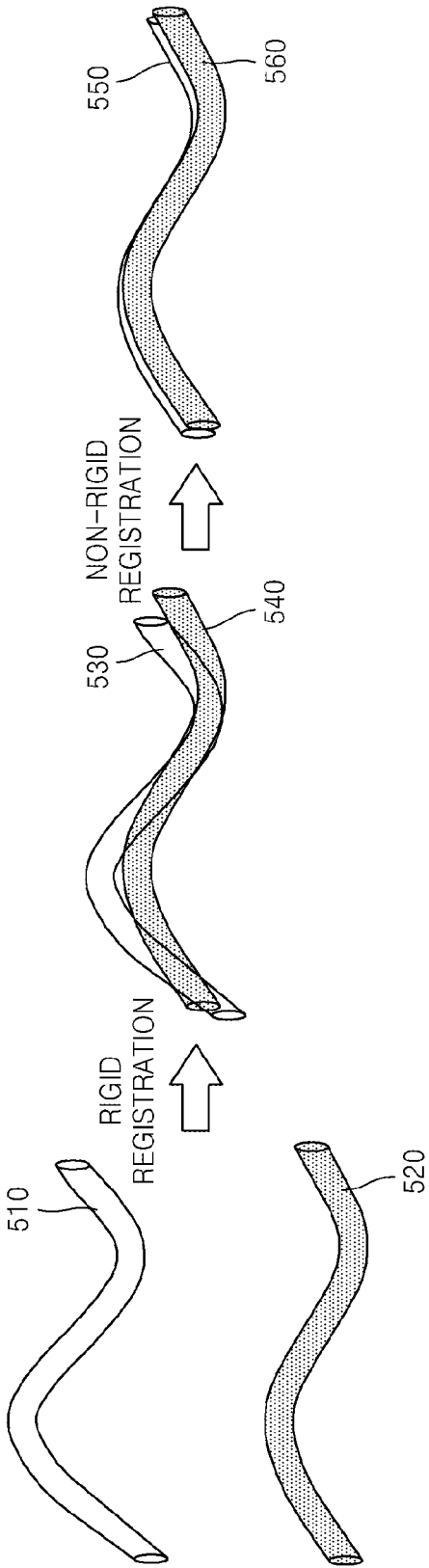
FIGS. 5A to 5C are diagrams illustrating conceptual schematic views of rigid registration and non-rigid registration which a characteristic point determining unit performs.

Referring to FIGS. 5A to 5C, reference numerals 510, 530, and 550 represent examples of a shape of a given part of a first model, and reference numerals 520, 540, 560 represent examples of a shape of a tissue corresponding to the given part of the first model that is extracted from a 3D ultrasound model. The figures shown in FIGS. 5A to 5C are just examples for explaining operations performed by the characteristic point determining unit 230 and do not mean shape information extracted from the first model or the 3D ultrasound image. Although reference numerals 510 to 560 of FIG. 5 are represented by figures formed from lines that are shape information extracted from the first model or the 3D ultrasound image, they may be a set of points that have a mesh shape.

First, referring to FIGS. 5A and 5B, the characteristic point determining unit 230 performs rigid registration of the first model with shape information. The characteristic point determining unit 230 roughly matches shape information 520 with a location of a first model 510 through rotation, scaling, and parallel translation of the shape information 520. For example, the characteristic point determining unit 230 may use an algorithm, such as, for example, an iterative closest point (ICP) algorithm to roughly match the shape information 520 with the location of the first model 510. In this case, the ICP algorithm is an algorithm that rotates, parallel-translates and scales some images with respect to one image to align subjects in a plurality of images. "Iterative point matching for matching of free-form curves and surfaces" (written by Zhengyou Zhang) provides a detailed description of the ICP algorithm.

Referring to FIG. 5B, if the characteristic point determining unit 230 performs only rigid registration, the first model 530 and the shape information may not be accurately matched. Thus, the characteristic determining unit 230 may perform non-rigid registration using a result of the rigid-registration to accurately match the first model with the shape information 540. The characteristic point determining unit 230 performs non-rigid registration by deforming characteristic points forming the shape information 540 to correspond to those forming the first model. For example, the characteristic point determining unit 230 may perform non-rigid registration using Expression 8 below.

$$\hat{A} = \underset{A}{\mathrm{argmin}} \sum_{x \in S} |f(x, A) - cl(x, T)| \qquad \text{Expression 8}$$

In Expression 8 above, the term $f(x, A)$ has a relation $$f(x, A) = \sum_{j=0}^{N} (w_j \varphi(\|x - y_j\|)) + c_0 + c_1 x_1 + c_2 x_2 + c_3 x_3 - x.$$

In this case, the parameter $A=\{w_0, \ldots, w_N, c_0, c_1, c_2, c_3\}$, and the parameter x means one of a set of points S to be deformed and matched, where $x=(x_1, x_2, x_3)$. For example, the parameter x means any one of a set of points forming the shape information 540 shown in FIG. 5B.

The term cI(x, T) means a coordinate of a point closest to a set of points T forming a model based on the parameter x. For example, the term cI(x, T) means a point closest to the parameter x among a set of points forming the first model 530 shown in FIG. 5B.

In the relation above, the term $\phi(\|x-y_j\|)$ is defined by Expression 9 below.

$$\phi(\|x-y_j\|) = -\exp(\|x-y_j\|) \qquad \text{Expression 9}$$

Referring to FIG. 5C, the characteristic point determining unit 230 may use a matched result of the first model 550 with the shape information 560 to obtain information about a characteristic point on a 3D ultrasound image corresponding to a characteristic point of the first model using the matched result of the first model 550 with the shape information 560. Information about the characteristic point means information about a location where a characteristic point exists on the 3D ultrasound image.

Referring back to FIG. 1, the characteristic point determining unit 230 transmits information about a determined characteristic point to the second model generating unit 240. The characteristic point determining unit 230 may also transmit information about the determined characteristic point to the storage unit 250.

The second model generating unit 240 uses an obtained characteristic point to generate a second model, which is an update of the first model. For example, the second model generating unit 240 may use information about the characteristic point transmitted from the characteristic point determining unit 230 to generate the second model that is an update of the first model transmitted from the storage unit 250.

First, the second model generating unit 240 uses external images (40 of FIG. 6) to calculate a physical property of a tissue that is included in a region of interest (30 of FIG. 6).

The second model generating unit 240 receives external images (40 of FIG. 6) from the storage unit 250 and calculates a physical property for a deformation of the first model. The physical property may be a property such as, for example what impact do forces applied to a specific tissue represented on the external image have on surrounding tissues or the physical property may be elasticity of a tissue. Subsequently, the second model generating unit 240 matches a characteristic point with a vertex of the first model. In this case, the characteristic point is one point on a 3D ultrasound image obtained by the characteristic point determining unit 230. For example, the second model generating unit 240 may use a result of the non-rigid registration to determine which point the characteristic point corresponds to among points forming the first model.

Subsequently, the second model generating unit 240 uses the matched result to generate the second model. For example, the second model generating unit 240 may reflect a physical property in the matched result to generate the second model that is an update of the first model.

Since the second model generating unit 240 calculates a physical property of a tissue that is included in a region of interest (30 of FIG. 6), it is possible to know how some points in the region of interest are deformed (e.g. where other points except for a characteristic point moves to) when any one point (e.g. a characteristic point) in the region of interest moves. Thus, the second model generating unit 240 may generate a second model in which information about the region of interest represented on a 3D ultrasound image is reflected on the basis of the first model. The information about the region of interest means changes in a shape and a location of the region of interest.

FIG. 6 is a diagram illustrating an example of an environment and system using a model generating system 1. The model generating system 1 includes a diagnostic ultrasound probe 10 and an image processing device 20. The model generating system 1 may further include an image display device 50 or a treatment-purpose ultrasound probe 60 (Ultrasound Probe). The model generating system 1 shown in FIG. 6 includes only components related to the present example. Thus, those skilled in the art may understand that general components other than those shown in FIG. 6 may be further included. For example, the model generating system 1 may include an interface unit (not illustrated). The interface unit may be responsible for inputting and outputting input information regarding a user and an image. The interface unit may include a network module for connection to a network and a universal serial bus (USB) host module for forming a data transfer channel with a mobile storage medium, depending on a function of the model generating system 1. In addition, the interface unit includes an input/output device such as a mouse, a keyboard, a touch screen, a monitor, a speaker, and a software module for running the input/output device.

In addition, the model generating system 1 shown in FIG. 6 may include the image processing device 20 shown in FIG. 1, and the descriptions that relate to FIG. 1 may also be applicable to the model generating system 1 shown in FIG. 6.

The Ultrasound Probe 60 radiates ultrasound waves for treatment such as high intensity focused ultrasound (HIFU), to a lesion in the region of interest 30 of a subject. The image processing device 20 may further include a treatment-purpose ultrasound generating unit (not shown) that generates ultrasound waves for treatment to radiate the ultrasound waves to a lesion using a generated second model. The Ultrasound Probe 60 may radiate the ultrasound waves for treatment to a lesion using a signal transmitted from the treatment-purpose ultrasound generating unit (not shown).

The image display device 50 displays a first model image, a 3D ultrasound image or a second model image that is generated from the image processing device 20. The image display device 50 includes all display devices, such as, for example, a display panel, as a liquid crystal display (LCD), a light-emitting diode (LED) display, a plasma display panel (PDP), a screen, a terminal, and a monitor that are provided at the model generating system 1. A screen may be a physical structure that includes one or more hardware components that provide the ability to render a user interface and/or receive user input. The screen can encompass any combination of display region, gesture capture region, a touch sensitive display, and/or a configurable area. The screen can be embedded in the hardware or may be an external peripheral device that may be attached and detached from the apparatus. The display may be a single-screen or a multi-screen display. A single physical screen can include multiple displays that are managed as separate logical displays permitting different content to be displayed on separate displays although part of the same physical screen. Information about the region of interest obtained from the image processing device 20 is provided to a user through the image display device 50, and may thus be used for recognizing a change in a status, a location, or a shape of a tissue.

Figure 7:
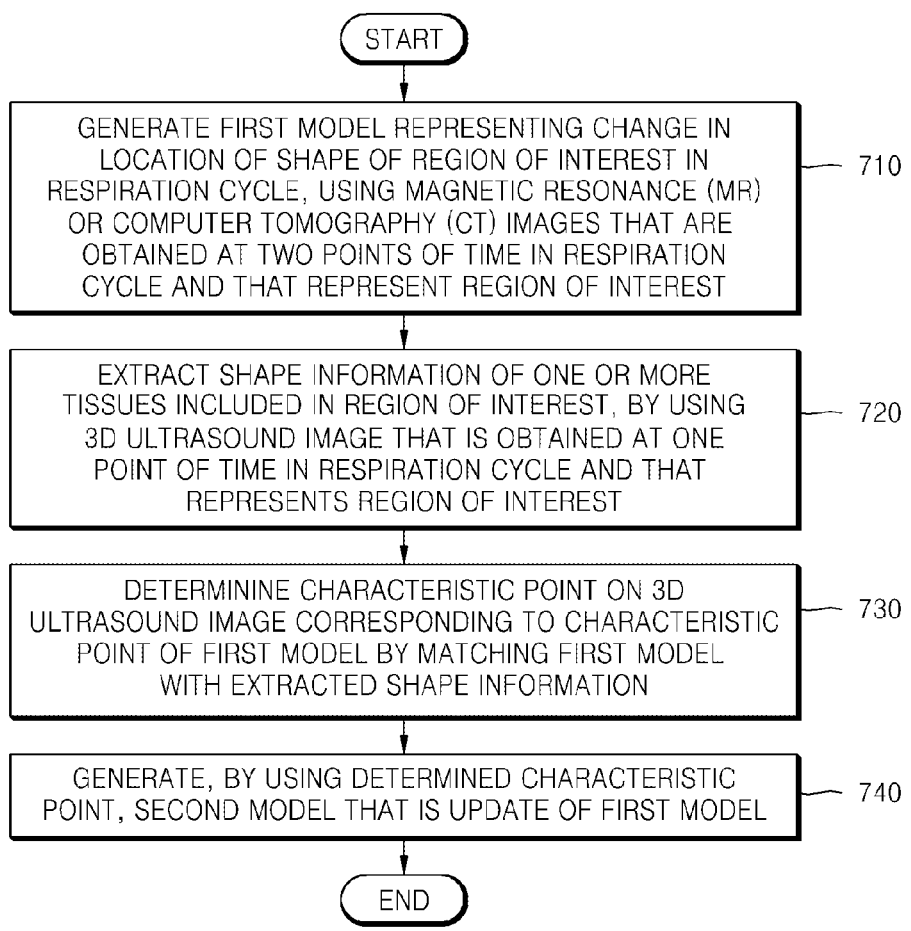
FIG. 7 is a diagram illustrating a method of generating a model representing changes in a shape and a location of a region of interest in a human body.

FIG. 7 is a diagrams illustrating a method of generating a model representing changes in a shape and a location of a region of interest in a human body. The operations in FIG. 7 may be performed in the sequence and manner as shown, although the order of some operations may be changed or some of the operations omitted without departing from the spirit and scope of the illustrative examples described. Many of the operations shown in FIG. 7 may be performed in parallel or concurrently.

Referring to FIG. 7, a method of tracking a change in an organ includes operations that are time-series processed by the image processing device 20 of FIG. 1 or the model generating system 1 of FIG. 6. Thus, descriptions provided above with respect to the image processing device 20 of FIG. 1 or the model generating system 1 of FIG. 6 may also be applicable to the method of generating the model of FIG. 7.

In operation 710, the first model generating unit 210 uses diagnostic images, such as MR images or CT images representing a region of interest 30 obtained at two points of time in a respiration cycle of a subject to generates a first model representing a change in a location of a shape of the region of interest 30 in the respiration cycle. In this case, the two points of time in the respiration cycle of the subject mean points of time with FI and FE in the respiration cycle.

In operation 720, the shape information extracting unit 220 uses a 3D ultrasound image representing the region of interest obtained at one point of time in the respiration cycle to extract shape information of one or more tissues, such as a diaphragm or a blood vessel, which are included in the region of interest 30. In addition, the shape information may include information about a thickness, a length, and a shape of the tissue. In addition, one point of time in the respiration cycle means a point of time when the external image is not precisely obtained.

In operation 730, the characteristic point determining unit 230 determines a characteristic point on the 3D ultrasound image corresponding to a characteristic point of a first model through the matching of the first model with the extracted shape information. The characteristic point determining unit 230 performs rigid registration of the first model with the shape information and performs non-rigid registration using a result of the rigid registration. The characteristic point determining unit 230 determines the characteristic point of the 3D ultrasound image using a result of the non-rigid registration.

In operation 740, the second model generating unit 240 uses the determined characteristic point to generate a second model that is an update of the first model.

As described above, the image processing device 20 may generate a model that accurately reflects a shape and a location of an organ in a human body that change according to a respiration cycle of a patient. In addition, since the image processing device 20 tracks a change of the organ using characteristics that may be clearly identified from the 3D ultrasound image, a noise-resistant track is possible. Because the image processing device 20 accurately tracks the change in the organ in a patient's body, depending on respiration, it is possible to enhance the accuracy of therapy and reduce a therapy time period if the device is applied to HIFU, radiation therapy, etc.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), CD-ROMs, magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

The apparatuses and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method, performed by a processor, of generating a model, the method comprising:
   generating a first model representing a change in the location or the shape of the region of interest during the respiration cycle, using diagnostic images that are obtained at two points of time in the respiration cycle and that represent the region of interest, wherein the diagnostic images are magnetic resonance (MR) images or computed tomography (CT) images or a combination thereof;
   extracting shape information of one or more tissues included in the region of interest at a shape information extractor, using a 3D ultrasound image that is obtained at one point of time in the respiration cycle;
   determining a characteristic point of the 3D ultrasound image corresponding to a characteristic point of the first model by matching the first model with the extracted shape information; and
   generating a second model by updating the first model with the determined characteristic point.

2. The method of claim 1, wherein the extracting of the shape information comprises performing a flatness test to determine whether the tissue is flat or a vesselness test to determine whether the tissue has a tube shape, and extracting shape information of the tissue from the 3D ultrasound image.

3. The method of claim 1, wherein the tissue comprises a diaphragm or a blood vessel.

4. The method of claim 1, wherein the determining of the characteristic point comprises:
   performing rigid registration on the first model and the extracted shape information;
   performing non-rigid registration by using a result of the rigid registration; and
   determining the characteristic point by using a result of the non-rigid registration.

5. The method of claim 1, wherein the generating of the second model comprises:
   calculating a physical property of a tissue included in the region of interest, using the diagnostic images;
   matching the characteristic point with a vertex of the first model, by using the physical property; and
   generating the second model by using a result of the matching.

6. The method of claim 1, wherein the generating of the first model comprises:
   segmenting surface information of the tissue that is represented on each of the diagnostic images; and
   performing interpolation by using the segmented surface information.

7. The method of claim 6, wherein the tissue comprises a lesion.

8. The method of claim 1, wherein the two points of time in the respiration cycle comprise a full inspiration time and a full expiration time.

9. A non-transitory computer readable recording medium having a program comprising instructions that perform the method of claim 1 when executed by a computer.

10. An apparatus, comprising a processor, for generating a model, the apparatus comprising:
    a first model generator configured to generate a first model representing a change in a location or a shape of a region of interest during a respiration cycle, using diagnostic images that are obtained at two points of time in the respiration cycle and that represent the region of interest, wherein the diagnostic images are magnetic resonance (MR) images or computed tomography (CT) images or a combination thereof;
    a shape information extractor configured to extract shape information of one or more tissues included in the region of interest, using a 3D ultrasound image that is obtained at one point of time in the respiration cycle;
    a characteristic point determiner configured to determine a characteristic point of the 3D ultrasound image corresponding to a characteristic point of the first model; and
    a second model generator configured to generate a second model by updating the first model with the determined characteristic point.

11. The apparatus of claim 10, wherein the shape information extractor is configured to perform a flatness test to determine whether the tissue is flat or a vesselness test to determine whether the tissue has a tube shape, and to extract shape information of the tissue from the 3D ultrasound image.

12. The apparatus of claim 10, wherein the tissue comprises a diaphragm or a blood vessel.

13. The apparatus of claim 10, wherein the characteristic point determiner is configured to perform rigid and non-rigid registration on the first model and the extracted shape information and to determine the characteristic point by using results of the rigid and non-rigid registration.

14. The apparatus of claim 10, wherein the second model generator is configured to calculate a physical property of a tissue included in the region of interest by using the diagnostic images, matches the characteristic point with a vertex of the first model by using the calculated physical property, and generate the second model using a result of the matching.

15. The apparatus of claim 10, wherein the first model generator is configured to segment surface information of a tissue that is represented on each of the diagnostic images and to perform interpolation by using the segmented surface information.

16. The apparatus of claim 15, wherein the tissue comprises a lesion.

17. The apparatus of claim 10, wherein the two points of time in the respiration cycle comprise a full inspiration time and a full expiration time.

18. The apparatus of claim 10, further comprising a storage configured to store the first model and the second model.

* * * * *